United States Patent
Leyde et al.

(12)

(10) Patent No.: US 6,693,431 B1
(45) Date of Patent: Feb. 17, 2004

(54) BATTERY SYSTEM AND METHOD OF DETERMINING BATTERY CONDITION

(75) Inventors: Kent W. Leyde, Redmond, WA (US); Daniel J. Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 722 days.

(21) Appl. No.: 09/141,707

(22) Filed: Aug. 28, 1998

(51) Int. Cl.[7] .............................................. G01N 27/416
(52) U.S. Cl. ....................................... 324/434; 324/435
(58) Field of Search ................................ 324/434, 430, 324/427, 435, 431; 320/116

(56) References Cited

U.S. PATENT DOCUMENTS

| | | | | |
|---|---|---|---|---|
| 4,259,639 A | | 3/1981 | Renirie .......................... 324/430 |
| 4,390,841 A | * | 6/1983 | Martin et al. ................ 324/427 |
| 4,725,784 A | | 2/1988 | Peled et al. .................. 324/427 |
| 5,065,084 A | | 11/1991 | Oogita ........................... 320/48 |
| 5,130,659 A | | 7/1992 | Sloan ........................... 324/435 |
| 5,162,741 A | | 11/1992 | Bates ........................... 324/431 |
| 5,250,905 A | * | 10/1993 | Kuo et al. .................... 324/435 |
| 5,483,165 A | * | 1/1996 | Cameron et al. ............ 324/427 |
| 5,596,278 A | | 1/1997 | Lin .............................. 324/435 |
| 5,598,101 A | | 1/1997 | Den Dekker |
| 5,607,454 A | | 3/1997 | Cameron et al. .............. 607/5 |
| 5,721,482 A | | 2/1998 | Benvegar et al. |

* cited by examiner

*Primary Examiner*—N. Le
*Assistant Examiner*—Vincent Q. Nguyen

(57) ABSTRACT

A battery system including a main battery cell having a first capacity; a sense battery cell connected in series with the main battery cell, the sense battery cell having a second capacity less than the first capacity; and a battery capacity indicator monitoring a parameter of the sense battery cell. A method of determining a battery condition in a battery operated device, the method including providing a battery system, the battery system comprising a main battery cell having a first capacity and a sense battery cell, the sense battery cell having a second capacity less than the first capacity, the main battery cell and the sense battery cell being coupled in series; monitoring a parameter of the sense battery cell; and determining a condition of the main battery cell from the monitored sense battery cell parameter.

23 Claims, 4 Drawing Sheets

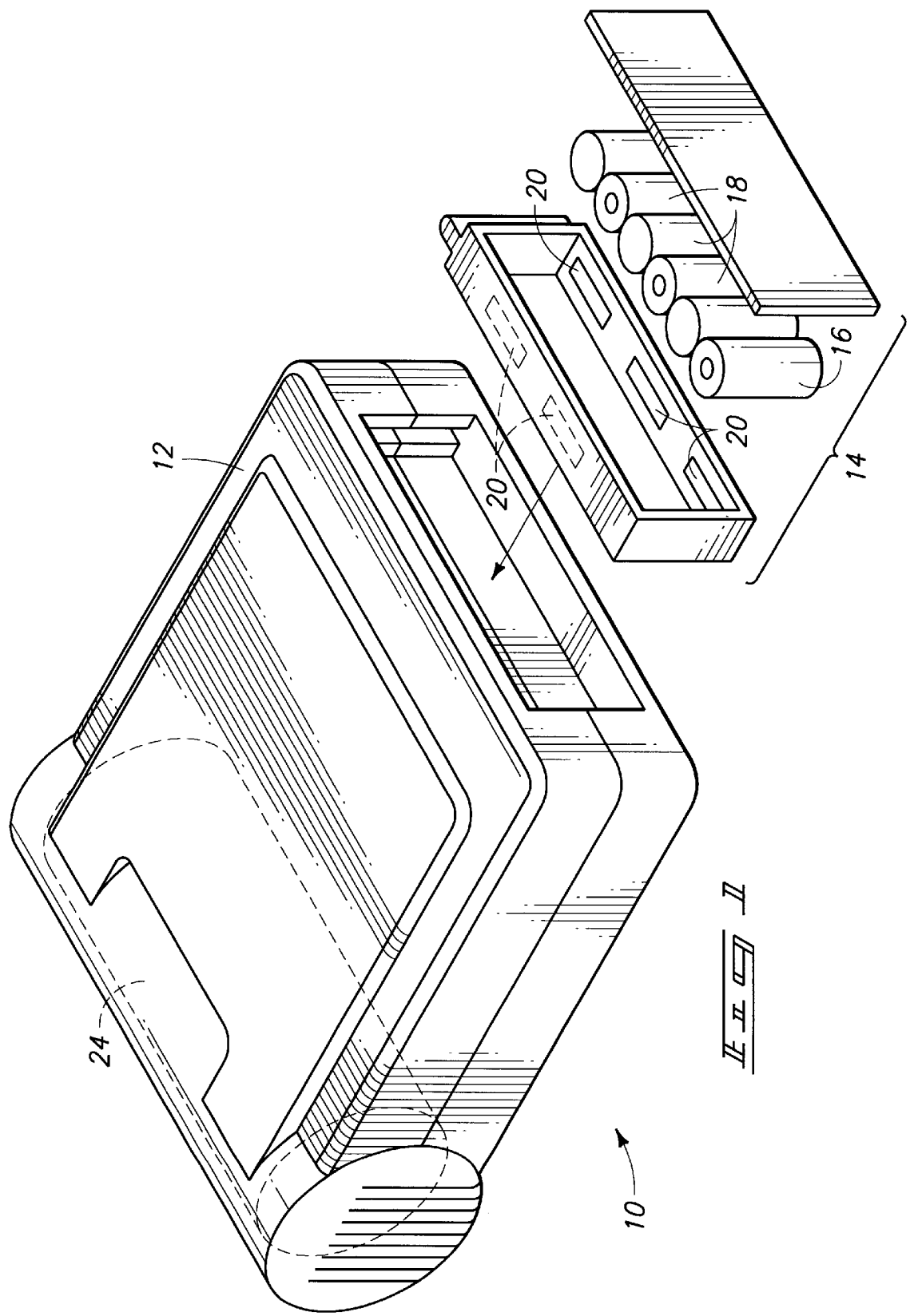

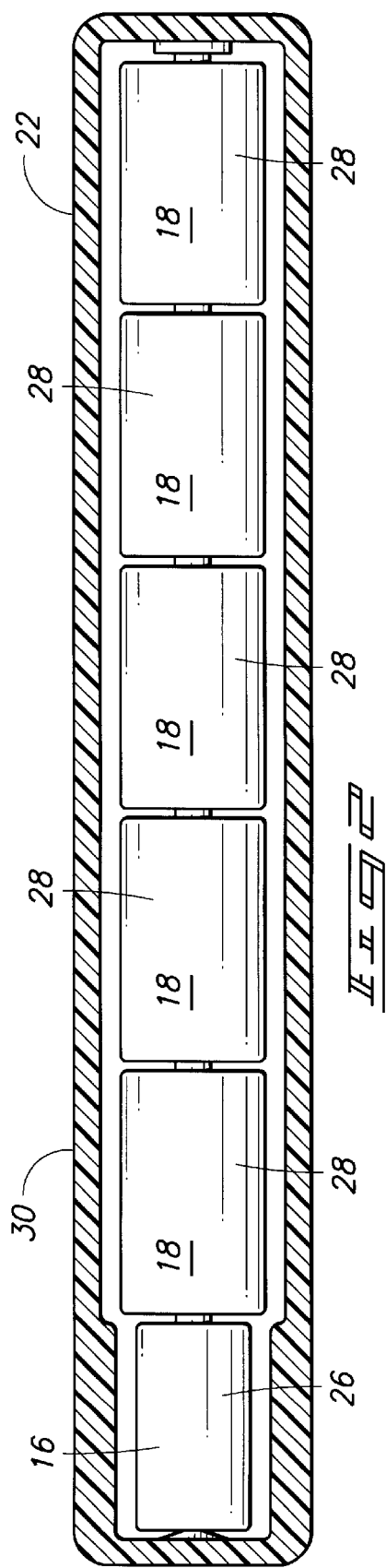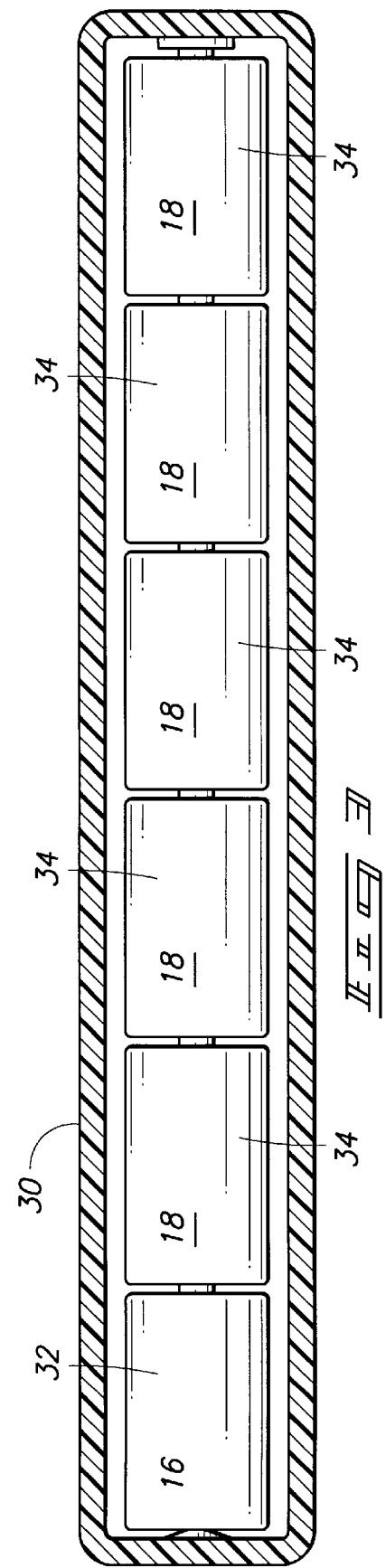

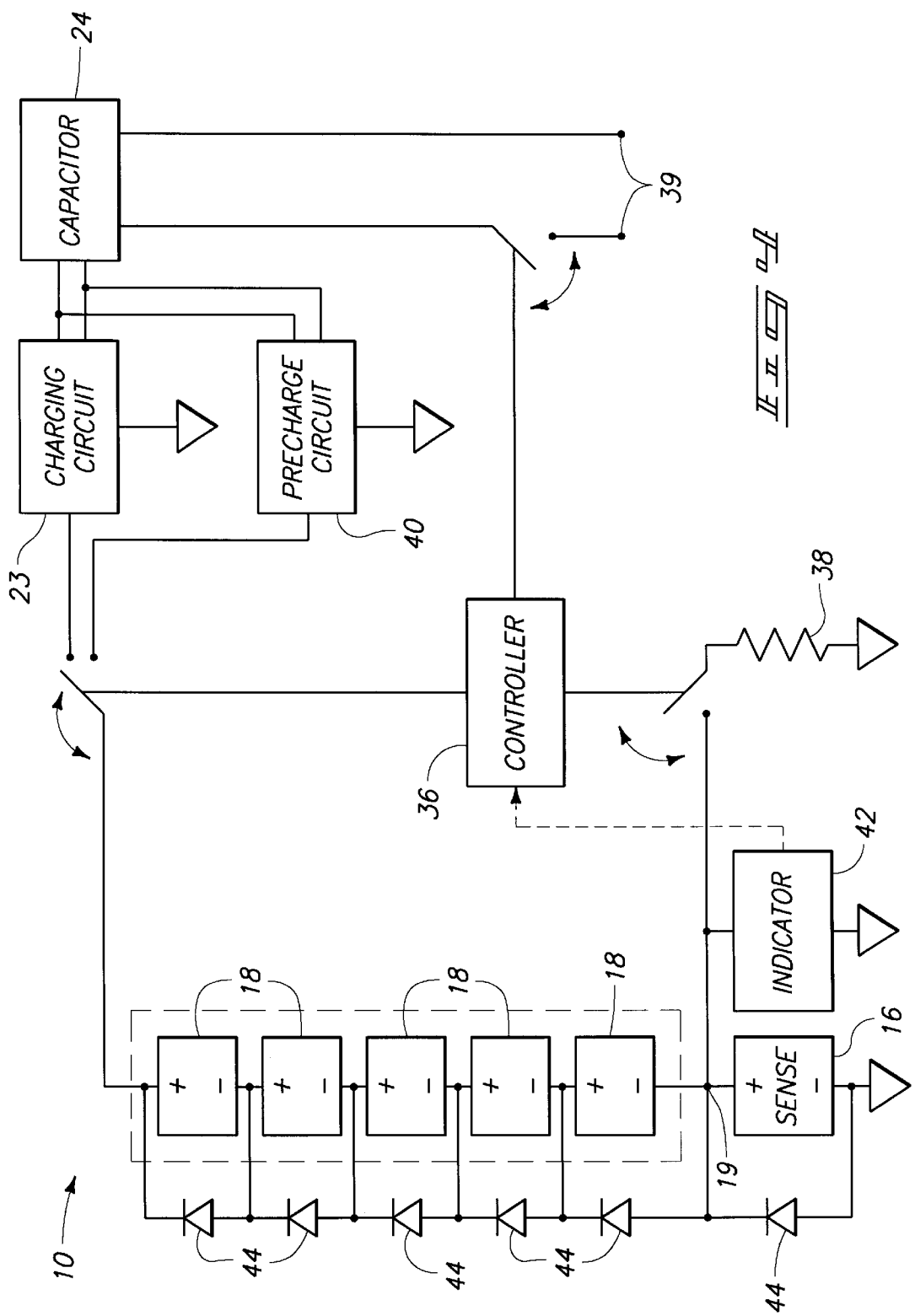

BATTERY SYSTEM AND METHOD OF DETERMINING BATTERY CONDITION

FIELD OF THE INVENTION

The invention relates to batteries and battery operated devices. More particularly, the invention relates to a method and apparatus for determining the condition of a battery. The invention also relates to a method and apparatus for detecting a low battery condition in a device that uses a battery.

BACKGROUND OF THE INVENTION

For battery powered devices, it is often useful to know the condition of the battery. More particularly, it is important to know when the battery is almost drained. This can be important in avoiding data loss or in avoiding loss of functionality while the device is being used. For example, failure to indicate a low battery condition of a battery operated computer could result in data loss if the remaining power is insufficient to save the information and exit the application. Battery operated devices are sometimes used in locations where replacement batteries are not readily available. Also, battery operated devices are sometimes used in applications where time required to change batteries can be too long. This is true, for example, with battery operated cameras, with medical devices, or other devices having time sensitive uses. Knowledge of the remaining battery capacity of a battery operated medical device could be crucial in a medical emergency.

Various battery condition detectors are known in the art. One type of battery condition detector keeps track of transfer of charge. Another type of battery condition detector keeps track of use time of the device. Keeping track of use time or charge transfer results in an inaccurate determination of battery condition. Batteries lose charge even when not in use. In addition, the battery's temperature can affect its capacity and useful life. Furthermore, monitoring the electrical characteristics of a battery, such as voltage or resistance, often does not provide enough information regarding the capacity of the battery.

Electrotherapy devices are used to provide an electric shock to treat patients for a variety of heart arrhythmias. For example, external defibrillators provide relatively high-level electric shocks to a patient, usually through electrodes attached to the patient's torso, to convert ventricular fibrillation ("VF") or shockable ventricular tachycardia ("shockable VT") to a normal sinus rhythm. Similarly, external cardioverters can be used to provide shocks to convert atrial fibrillation to a more normal heart rhythm. Many electrotherapy devices are powered by batteries. Reliably indicating a low battery condition well before depletion is critically important in electrotherapy devices.

Prior art electrotherapy devices provide an indication of a low battery condition and a depleted battery condition. Stopping an electrotherapy treatment to replace a battery can have a detrimental effect on the patient being treated. Many prior art electrotherapy devices fail to reliably indicate battery depletion. The actual amount of battery capacity remaining when prior art devices indicate a low battery condition can vary with the ambient temperature, battery manufacturing variances, battery discharge history, battery recharge history, etc.

Battery capacity detectors and indicators are known in the art. Most prior art battery capacity indicators are based on one or both of the following two methods: (1) measurement of a battery parameter, and (2) cumulative measurement of battery output. The measurements are typically made in absolute, not relative, terms. The prior art battery capacity indicators also sometimes include some way to compensate for the environmental effects of time and temperature.

One approach is shown in U.S. Pat. No. 5,250,905 to Kuo et al. The Kuo et al. patent discloses a battery capacity indicator for a primary battery, such as a standard alkaline "AA" battery, in which a much smaller indicator battery is connected in parallel to the main battery. The indicator battery is designed to have a much lower capacity and a correspondingly much higher impedance than the main battery. The anode of the indicator battery disappears during use, revealing a message such as "Replace" when the indicator battery and the main battery have discharged to the point where the main battery is nearly depleted. Because the indicator battery is very different from the main battery in design and composition, it is difficult to match the indicator battery and the main battery so the main battery is nearly depleted when the "Replace" message appears.

U.S. Pat. No. 5,596,278 to Lin discloses a condition indicator assembly including an electrochemical indicator battery connected in series to an auxiliary battery. The condition indicator assembly is connected in parallel to a main battery being tested.

U.S. Pat. No. 5,483,165 to Cameron et al. discloses a battery system and method in which a sense battery is substantially identical to, and connected in series with, the main battery. A predetermined additional load is placed on the sense battery to discharge it at a higher rate than the main battery. The voltage of the sense battery is monitored to determine when it is nearly depleted. A predetermined amount of capacity will remain on the main battery at this point. One drawback of the Cameron et al. approach, however, is the extra circuitry needed to accelerate the discharge of the sense battery.

Other battery capacity indicators are shown in U.S. Pat. No. 4,259,639 to Remirie; U.S. Pat. No. 4,725,784 to Peled et al.; U.S. Pat. No. 5,162,741 to Bates; U.S. Pat. No. 5,065,084 to Oogita; and U.S. Pat. No. 5,130,659 to Sloan.

The specifications of the patents described above, as well as those referenced below, are hereby incorporated herein in their entirety by reference.

SUMMARY OF THE INVENTION

The invention provides a battery system having a sense battery cell with a smaller capacity than a main battery cell.

One aspect of the invention provides a battery system including a main battery cell, a sense battery cell connected in series with the main battery cell, and a battery capacity indicator monitoring a parameter of the sense battery cell. The sense battery cell has a capacity less than the main battery cell's capacity.

Another aspect of the invention provides a method of determining a battery condition in a battery operated device. The method comprises providing a battery system. The battery system includes a main battery cell and a sense battery cell. The sense battery cell has a capacity less than the main battery cell's capacity. The main battery cell and the sense battery cell are connected in series. A parameter of the sense battery cell is monitored. A condition of the main battery cell is determined from the monitored sense battery cell parameter.

DESCRIPTION OF THE DRAWINGS

FIG. 1 is a partially exploded perspective view of a battery operated device embodying the system.

FIG. 2 is a front view of a battery receptacle housing batteries in accordance with an embodiment of the invention.

FIG. 3 is a front view of a battery receptacle housing batteries in accordance with another embodiment of the invention.

FIG. 4 is a circuit schematic of a system according to one embodiment of the invention, which could be used with the battery shown in FIG. 3.

DETAILED DESCRIPTION OF THE INVENTION

Figure 5:
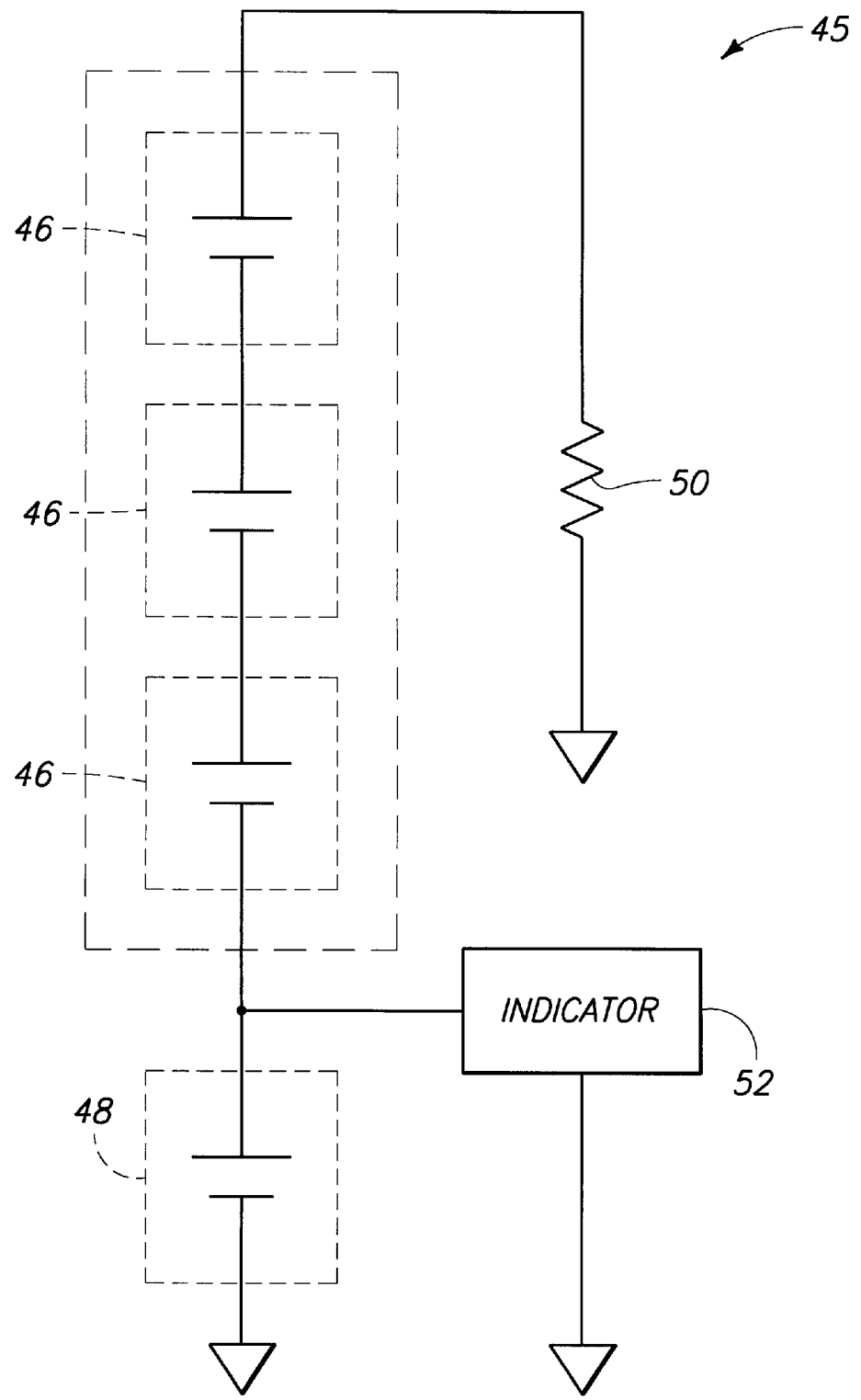
FIG. 5 is a schematic block drawing of a battery system according to one embodiment of this invention, which could be used with the battery shown in FIG. 2.

FIG. 1 shows a battery powered defibrillator 10 employing the invention. While other embodiments are possible, in the illustrated embodiment, the battery powered device 10 is a medical device such as a portable external defibrillator.

Still more particularly, in one embodiment, the battery powered device is a portable external defibrillator such as the defibrillator shown in U.S. Pat. No. 5,607,454 to Cameron et al. This defibrillator 10 is a portable semi-automatic external defibrillator ("AED") that delivers a therapeutic pulse of energy, such as a truncated exponential biphasic waveform. In order to ensure that the delivered shock will be within the optimum tilt range for a wide variety of patients, in one embodiment, this AED adjusts the characteristics of the therapeutic waveform in response to a real-time measurement of a patient-dependent electrical parameter. For example, high impedance patients receive a low-tilt waveform that is more effective per unit of delivered energy, and low impedance patients receive a high-tilt waveform that delivers more of the stored energy as described in Cameron (U.S. Pat. 5,607,454).

Although the invention is being described with respect to an AED, the invention is capable of being carried out in other medical devices, as well as in devices that use battery cells in general, as will become readily apparent from the following description.

The defibrillator 10 includes a housing 12. The defibrillator 10 further includes a battery receptacle 14 sized to removably receive and couple together at least one sense battery cell 16 and one or more main battery cells 18. FIG. 1, for illustration but not for limitation, shows a plurality of main battery cells 18; however, there may be as few as one main battery cell 18. In one embodiment, the battery receptacle 14 is removably received in the housing 12. In another embodiment (not shown), the battery receptacle 14 is integrally formed with or non-removable from the housing 12. The main battery cells 18 respectively have a capacity greater than the capacity of the sense battery cell 16.

The battery receptacle 14 couples the battery cells 16 and 18 in electrical series with one another. The battery cells 16 and 18 respectively have positive terminals and negative terminals. In one embodiment, the battery receptacle 14 includes conductive strips 20 coupling adjacent battery cells in series. For example, the receptacle 14 includes a conductive strip 20 coupling the negative terminal of a battery cell 16 or 18 to a positive terminal of an adjacent battery cell 16 or 18. The conductive strips 20 couple battery cells in series with adjacent battery cells to provide a series connection with a voltage defined by the sums of the voltages of the battery cells that are coupled together.

In one embodiment (FIG. 2), a battery receptacle 22 is configured to receive the battery cells 16 and 18 such that at least some of the battery cells 16 and 18 have battery terminals in contact with one another. More particularly, one or more pairs of adjacent battery cells 16 or 18 have battery cell terminals in contact with one another to provide a series connection. A tap 19 (FIG. 4) connects between the sense battery cell 16 and the main battery cell 18 so a parameter of the sense battery cell 16 can be measured.

In one embodiment, the battery cells 16 and 18 are rechargeable. In the illustrated embodiment, however, the battery cells are primary batteries. In another embodiment, the sense battery cell 16 has a chemistry type, and the main battery cells 18 respectively have a chemistry type that is the same as the chemistry type of the sense battery cell 16. For example, the sense battery cell 16 and main battery cells 18 are lithium manganese dioxide batteries. The illustrated embodiment uses lithium manganese dioxide primary battery cells instead of rechargeable battery cells. Primary battery cells have greater energy density than rechargeable battery cells, are cheaper and lighter, and are easier to maintain. While primary battery cells also have lower power and energy characteristics, use of a truncated exponential biphasic waveform permits operation at lower power levels.

In one embodiment, the sense battery cell 16 and the main battery cells 18 are all from the same source. In the illustrated embodiment, the sense battery cell and the main battery cells are all manufactured by the same manufacturer. Ideally, the battery cells 16 and 18 belong to the same manufacturing lot. Alternatively, the battery cells 16 and 18 are manufactured on the same date. In one embodiment, the sense battery cell 16 is identical in manufacturing lot to the main battery cells 18. The battery receptacle 14 or 22 receives the sense battery cell 16 plus the main battery cells 18 packaged in close proximity so that all of the battery cells 16 and 18 are exposed to substantially the same environmental conditions. The output of the sense battery cell 16 and main battery cells 18 combine to provide power to a system load of the battery operated defibrillator 10, such as to a charging circuit 23 for charging a capacitor 24 in the defibrillator embodiment (FIG. 4).

In the embodiment of FIG. 2, the receptacle 22 is sized to receive a sense battery cell 16 having a first size, and main battery cells 18 having respective second sizes different from the first size. More particularly, the receptacle 22 is sized to receive a sense battery cell 16 having a first capacity, and main battery cells 18 having respective second capacity different from the first capacity. The main battery cells 18 may have housings of the same general shape or of different shapes than the sense battery cell 16. In the illustrated embodiment, the receptacle 22 is sized to receive a sense battery cell 16 including a cylindrical outer surface 26 having a first diameter, and main battery cells 18 including respective cylindrical outer surfaces 28 having a second diameter different from the first diameter. For example, the sense battery cell may be a "C" battery while the main battery cells are "D" battery cells. As will be appreciated, the "C" battery has a lower capacity than the "D" battery cells, so by monitoring the condition of the "C" type battery, an indication of low battery capacity can be given before the "D" type battery cells are completely discharged. As will be appreciated by those skilled in the art, many different sizes of batteries may be combined to form the main battery cells and the sense battery cells.

In another embodiment (FIG. 3), a receptacle 30 is sized to receive a sense battery cell 16 having a first capacity, and main battery cells 18 respectively having a second capacity that is the same as the first capacity. The main battery cells 18 have housings of the same size and shape as the sense battery cell 16. For example, the receptacle 30 is sized to receive a sense battery cell 16 including a cylindrical outer surface 32 having a first diameter, and main battery cells 18 including respective cylindrical outer surfaces 34 having a second diameter the same as the first diameter. In this embodiment, the sense battery cell 16 is pre-discharged by a certain amount before the battery cells are inserted into the battery receptacle.

In another embodiment, the discharging is performed by coupling the sense battery cell 16 to a load external of the defibrillator 10 such as a resistor, for a predetermined amount of time. In another embodiment (FIG. 4), this discharging is performed by the defibrillator 10 itself For example, a controller 36 in the device 10 selectively couples the sense battery cell 16 to a load 38 for a predetermined amount of time, until a predetermined amount of charge passes through the load 38, or until the voltage of the sense battery cell falls below a predetermined threshold higher than the predetermined threshold for indicating low battery capacity. In at least this embodiment, the sense battery cell 16 has the same initial charge as each of the main battery cells, prior to the pre-discharging of the sense battery cell.

The controller 36 in the housing is configured to control selective delivery of a defibrillation shock using power from the sense battery cell 16 and the main battery cells 18. The defibrillator 10 comprises an energy source to provide a voltage or current pulse at output electrodes 39. In the illustrated embodiment, the energy source is the capacitor 24. In an alternative embodiment, a capacitor bank is arranged to act as a single capacitor.

In one embodiment, the defibrillator 10 further includes a capacitor pre-charge circuit 40, as described in Cameron (U.S. Pat. No. 5,607,454), to charge the capacitor 24 using the battery cells 16 and 18. More particularly, the capacitor pre-charge circuit 40 and controller 36 begins charging the capacitor 24 as soon as the defibrillator is activated, even before VF or shockable VT (and the need for defibrillation) has been detected. The precharge voltage level is kept below the level where damage to the defibrillator, the patient, or the operator, could occur in the event of a single fault. Thus, for example, whereas in one embodiment the full preshock capacitor voltage is 1650 Volts, the precharge level is 1100 Volts (or about one third lower than full charge voltage). This precharge procedure minimizes the amount of energy that needs to be transferred from the battery to the capacitor when a therapeutic shock is indicated, thereby reducing the required size of the battery cells.

The defibrillator 10 further comprises the indicator 42, supported by the housing, that couples to the sense battery cell 16 after the sense battery cell is inserted. The indicator 42 indicates the condition of the sense battery cell 16. For example, in one embodiment, the indicator 42 that is employed to indicate the condition of the sense battery cell is similar to that described in Cameron (U.S. Pat. No 5,483,165). In the illustrated embodiment, the indicator 42 includes thresholding circuitry, such as circuitry including an op-amp, to generate a signal if the voltage of the sense battery cell 16 falls below a predetermined threshold. A diode 44 is connected around the sense battery cell 16 to permit the main battery cells 18 to be used after the sense battery cell 16 has been depleted. Diodes 44 may also be similarly connected around respective main battery cells 18.

FIG. 5 shows a battery system 45 according to a more general embodiment of this invention. The battery system has one or more main battery cells 46. FIG. 5, for illustration but not for limitation, shows a plurality of main battery cells 46; however, there may be as few as one main battery cell 46. The main battery cells 46 may be, e.g., standard alkaline battery cells or any other type of off-the-shelf or custom battery cells.

Connected in series with main battery cells 46 in the battery system is at least one sense battery cell 48. The main battery cells 46 and sense battery cell 48 together provide power to a load 50, as shown. The sense battery cell 48, however, has a capacity that is less than that of respective main battery cells 46 by a predetermined amount. In one embodiment, for example, each of the main battery cells 46 are standard "D" type battery cells, (rated at 7 A-hrs) while the sense battery cell 48 is a standard "C" type battery cell (rated at 3.5 A-hrs).

In another embodiment, for example, the sense battery cell 48 and each of the main battery cells 46 are substantially identical, such as all "D" battery cells or all "C" battery cells. In this embodiment, the sense battery cell 48 is discharged by a predetermined amount prior to use of the battery system; i.e., prior to providing power from battery cells 46 and 48 to load 50.

Because the main battery cells 46 and the sense battery cell 48 are connected in series, and because the capacity of sense battery cell 48 is less than the capacity of respective main battery cells 46, the sense battery cell 48 will be depleted before the main battery cell 46. A battery capacity indicator 52 monitors an electrical parameter of sense battery cell 48 and determines the condition (e.g., capacity available or depleted) of the sense battery cell 48 from the monitored parameter. When sense battery cell 48 is depleted, the battery capacity indicator 52 may indicate a low battery condition for main battery cells 48 visually and/or audibly.

Because of the preset capacity relationship between the main battery cell and the sense battery cell, the remaining capacity of the main battery cell at the point where the sense battery cell is depleted and the low battery warning is given can be predicted. As discussed above, this feature of the invention is useful in situations in which foreknowledge of remaining battery capacity and impending battery depletion is important, such as in the use of electrotherapy devices.

Modifications to the invention described above will be apparent to those skilled in the art. Such modifications are within the scope of this invention. For example, one embodiment of the invention is a method of manufacturing a battery-powered device. The method includes removably receiving and coupling together in series a sense battery cell having a first capacity and a main battery cell having a second capacity greater than the first capacity, and providing circuitry to indicate a low battery condition if the voltage of the sense battery cell falls below a predetermined threshold. This method may also include removably receiving and coupling together in series a sense battery cell and multiple main battery cells having the second capacity. In addition, the circuitry may be coupled to the sense battery cell after the sense battery cell is received by the battery-powered device. Furthermore, the main battery cell may be rechargeable, or the sense and main battery cells may have the same chemistry type. For example, the sense and main battery cells may be lithium manganese dioxide batteries. Moreover, the sense and main batteries may each have the same physical size, i.e., occupy the same respective volumes.

What is claimed is:

1. A battery system operable to provide energy to a load, the battery system comprising:

a main battery cell having a first maximum charge-storage capacity and storing a charge;

a sense battery cell coupled in series with the main battery cell and having a second maximum charge-storage capacity that is less than the first charge-storage capacity; and a battery-charge indicator operable to monitor a parameter of the sense battery cell and to determine the charge on the main battery cell from the monitored parameter.

2. The battery system of claim 1 wherein the battery system further comprises a plurality of additional main battery cells coupled in series with the sense battery cell.

3. The battery system of claim 1 wherein the main and sense battery cells arc lithium manganese dioxide battery cells.

4. The battery system of claim 1 wherein the sense battery cell stores a smaller charge than the main battery cell before an initial, simultaneous discharge of the main and sense battery cells through the load.

5. The battery system of claim 1 wherein the main and sense batteries are lithium manganese dioxide batteries.

6. The battery system of claim 1 wherein the monitored parameter comprises a voltage across the sense battery cell.

7. A battery-operated device, comprising:

a housing configured to removably receive and serially couple together a sense battery cell having a first maximum charge-storage capacity and a main battery cell having a second maximum charge-storage capacity that is greater than the first maximum charge-storage capacity; and circuitry coupled to the sense battery cell and configured to indicate a low main-battery condition based on a parameter of the sense battery cell.

8. The battery-operated device of claim 7 wherein the housing is configured to removably receive and couple together the sense battery cell and a plurality of main battery cells.

9. The battery-operated device of claim 7, further comprising the sense battery cell and the main battery cell in the housing.

10. The battery-operated device of claim 7 wherein the main battery cell is rechargeable.

11. The battery-operated device of claim 7 wherein the sense and main battery cells have a same chemistry type.

12. The battery-operated device of claim 7 wherein the sense battery cell and the main battery cell are lithium manganese dioxide battery cells.

13. The battery-operated device of claim 7, further comprising circuitry coupled to the housing and configured to generate a defibrillation shock using power from the serially coupled sense and main battery cells.

14. A method comprising:

monitoring a parameter of a sense battery cell having a first maximum charge-storage capacity, the sense battery cell serially coupled to a main battery cell having a charge and a second maximum charge-storage capacity that is larger than the first charge-storage capacity; and determining the charge on the main battery cell from the monitored parameter of the sense battery cell.

15. The method of claim 14 wherein additional main battery cells are connected in series with the sense battery cell.

16. The method of claim 15 wherein a battery terminal of one of the main battery cells is in contact with a battery terminal of another one of the main battery cells.

17. The method of claim 14, further comprising indicating the charge on the main battery cell after the determining of the charge.

18. The method of claim 14, further comprising:

powering a load with the serially coupled main and sense battery cells; and partially discharging the sense battery cell a predetermined amount before the powering of the load.

19. The method of claim 14, further comprising:

serially coupling the main and sense battery cells; and partially discharging the sense battery cell a predetermined amount before serially coupling the main and sense battery cells.

20. The method of claim 14 wherein the main and sense battery cells each comprise a respective lithium manganese dioxide battery cell.

21. The method of claim 14 wherein the main and sense battery cells each comprise a respective rechargeable battery cell.

22. A method, comprising:

initially powering a load with a series combination of a sense battery cell and a main battery cell, the sense battery cell having a smaller maximum charge-storage capacity than the main battery cell and determining the charge on the main battery cell from the sense battery cell.

23. The method of claim 22 further comprising partially discharging the sense battery cell before initially powering the load.

* * * * *